United States Patent [19]

Vogel et al.

[11] Patent Number: 5,488,147
[45] Date of Patent: Jan. 30, 1996

[54] DIARYLIODONIUM FLUOROALKYL SULFONATE SALTS AND A METHOD OF MAKING

[75] Inventors: Dennis E. Vogel; Kim M. Vogel, both of Lake Elmo, Minn.

[73] Assignee: Minnesota Mining and Manufacturing Company, Saint Paul, Minn.

[21] Appl. No.: 278,139

[22] Filed: Jul. 21, 1994

[51] Int. Cl.⁶ .................................................. C07C 303/32
[52] U.S. Cl. .................................................... 562/113
[58] Field of Search ............................................ 562/113

[56] References Cited

U.S. PATENT DOCUMENTS

| | | | |
|---|---|---|---|
| 3,981,897 | 9/1976 | Crivello | 260/440 |
| 4,136,102 | 1/1979 | Crivello | 260/440 |
| 4,151,175 | 4/1979 | Crivello et al. | 260/326.26 |
| 4,238,394 | 12/1980 | Crivello et al. | 260/326.26 |
| 4,329,300 | 5/1982 | Crivello et al. | 260/440 |
| 4,348,525 | 9/1982 | Koser et al. | 546/346 |
| 4,399,071 | 8/1983 | Crivello et al. | 260/440 |
| 4,529,490 | 7/1985 | Crivello et al. | 204/159.11 |
| 4,786,441 | 11/1988 | Miller | 260/513 |
| 4,826,635 | 5/1989 | Koser et al. | 260/545 |
| 4,992,571 | 2/1991 | Fukuyama et al. | 556/64 |
| 5,073,643 | 12/1991 | Crivello | 556/64 |
| 5,079,378 | 1/1992 | Crivello | 556/64 |
| 5,277,767 | 1/1994 | Cushman et al. | 204/59 |

FOREIGN PATENT DOCUMENTS

| | | | |
|---|---|---|---|
| 0119068A1 | 9/1984 | European Pat. Off. | C07C 25/00 |

OTHER PUBLICATIONS

Beringer et al, JACS 80 (1958), 4279.
Research Disclosure (anonymous author) 35042 p. 390.
Beringer, F. M. et al., "J. Am. Chem. Soc." vol. 75, (Jun. 5, 1953) pp. 2705–2712.
Stang, P. J. et al., "Tetrahedron Lett." vol. 33, No. 11, (1992) pp. 1419–1422.
Masson, I. et al., "J. Chem. Soc." (1937) pp. 1718–1723.
Crawford, R. et al., "J. Am. Chem. Soc." vol. 78, (Aug. 5, 1956) pp. 3819–3820.
Beringer, F. M. et al., "J. Am. Chem. Soc." vol. 80, (Aug. 20, 1958), pp. 4279–4281.
Mason, I., "Nature" vol. 139, (Jan. 23, 1937) pp. 150–151.
Crivello et al., "Macromolecules", vol. 10, No. 6, (Nov.–Dec. 1977) pp. 1307–1315.
Crivello et al., "J. Poly. Sci. Symp.", vol. 56, (1976) pp. 383–395.
Beringer, F. M. et al., "J. Am. Chem. Soc.", vol. 81, (Jan. 20, 1959) pp. 342–361.
Research Disclosure, vol. 350042, (Jun. 1993) p. 390.
Dektar, J. L.; Hacker, N. P., "J. Org Chem.", vol. 55, (1990) pp. 639–647.
Stang, P. J. et al., "Heterocyclic Chem.", vol. 29, (Jul. 1992) pp. 815–818.
Koser, G. F., "J. Org. Chem.", vol. 45, (1980) pp. 1543–1544.
Stang, P. J., "Tetrahedron Letters", vol. 32, No. 51, (1991), pp. 7497–7498.
Dalziel, J. R., "Inorg. Chem.", vol. 15, No. 6, (Jun. 1976) pp. 1247–1251.
Kitamura, T. et al., "Synthesis", vol. 10, (Oct. 1992) pp. 945–946
Sager, W. F., "Phys. Org. Chem.", vol. 2, (1964) pp. 323–400.

*Primary Examiner*—Jose G. Dees
*Assistant Examiner*—Joseph M. Conrad, III
*Attorney, Agent, or Firm*—Gary L. Griswold; Walter N. Kirn; Janice L. Dowdall

[57] ABSTRACT

The present invention provides a convenient, simple, safe and efficient one-pot method for the synthesis of a number of diaryliodonium triflate salts which does not involve sulfuric acid and which eliminates the need for any counter-ion exchange processes.

The invention also provides a novel salt of the formula

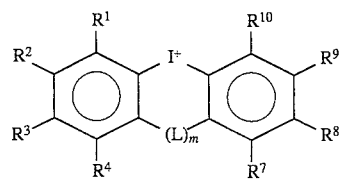

16 Claims, No Drawings

DIARYLIODONIUM FLUOROALKYL SULFONATE SALTS AND A METHOD OF MAKING

FIELD OF THE INVENTION

This invention relates to a method for preparing diaryliodonium fluoroalkyl sulfonate salts by a one-pot process which does not involve counter ion exchange, and to salts made by the method. Preferably, the salts are diaryliodonium trifluoromethanesulfonate ("triflate") salts. The invention also relates to certain novel diaryliodonium fluoroalkyl sulfonate salts themselves.

BACKGROUND OF THE INVENTION

Iodonium salts are important components of many imaging systems. They are useful for in-situ photochemical production of strong protic acids or free radical species which are subsequently used to initiate polymerizations or depolymerizations, or to react with an acid-sensitive functionality. Generally, they are thermally stable and photochemically labile, which is an ideal situation for imaging applications such as printing plates, lithographic films, and proofing systems, as well as for curing of, e.g., epoxide-type resins.

Symmetrical iodonium salts known in the art are commonly prepared by coupling an aromatic compound with iodate (e.g., potassium iodate), acetic anhydride, and sulfuric acid to yield a diaryliodonium bisulfate salt (See Crivello U.S. Pat. Nos. 3,981,897; 4,136,102; 4,151,175; 4,238,394; and 4,529,490 (assigned to General Electric); Beringer, F. M.; Drexler, E. M.; Gindler, E. M.; Lumpkin, C. C. *J. Am. Chem. Soc.* 1953, vol. 75, p. 2705; Beringer, F. M.; Falk, R. A.; Karniol, M.; Lillien, I.; Masullo, G.; Mausner, M.; Sommer, E. *ibid* 1959, vol. 81, p. 342; Klemm, E.; Alkahini, G.; Timpe, H. J. DD 290651; Crivello, J. V.; Lam, J. H. W.; Volante, C. N.; et al. *J. Radiat. Curing* 1977, vol. 4, p. 2; Crivello, J. V.; Lam, J. H. W. *J. Polym. Sci. Symp.* 1976, vol. 56, p. 383; and Crivello, J. V.; Lam, J. H. W. *Macromolecules* 1977, 10, 1307). Diaryliodonium bisulfate salts are generally too insoluble and unreactive to be of direct utility, and must be converted to other counter ions, typically by ion exchange procedures. A number of additional methods of preparing symmetrical and unsymmetrical diaryliodonium salts are known; most of them require the use of strong acids. (See Mason, I. *Nature* 1937, vol. 139, p. 150; Masson, I.; Race, E. *J. Chem Soc.* 1937, p. 1718; Masson, I.; Hanby, W. E. ibid. 1937, p. 1699; Masson, I. Argument, C. ibid. 1938, p. 1702; Beringer, F. M.; Bachofner, H. E.; Falk, R. A.; Leff, M. *J. Amer. Chem. Soc.* 1958, vol. 80, p. 4279; Collette, J. D.; McGreer, D.; Crawford, R.; Chubb, R.; Sandin, R. B. *J. Amer. Chem. Soc.* 1956, vol. 78, p. 3819; JP 63005040 Jan. 11, 1988; EP 119068; Crivello, J. V.; Lee, J. L. U.S. Pat. No. 4,399,071; Fukuyama, J. M.; Lee, J. L., Crivello, J. V. U.S. Pat. No. 4,992,571; Dektar, J. L.; Hacker, N. P. *J. Org. Chem.* 1990, vol. 55, p. 639; Research Disclosure RD 350042 1993; Crivello, J. V. U.S. Pat. No. 4,329,300 (May 11, 1982); Koser, G. F.; Wettach, R. H.; Smith, C. S. *J. Org. Chem.* 1980, vol. 45, p. 1543; Koser, G. F.; Wettach, R. H. U.S. Pat. No. 4,348,525 (Sep. 7, 1982); Koser, G. F.; Wettach, R. H. U.S. Pat. No. 4,826,635 (May 2, 1989); Crivello, J. V. U.S. Pat. No. 5,073,643 (Dec. 17, 1991); Crivello, J. V. U.S. Pat. No. 5,079,378 (Jan. 7, 1992); Kitamura, T.; Matsuyuki, J-i.; Nagata, K.; Furuki, R.; Taniguchi, H. *Synthesis,* 1992, vol. 10, p. 945; Dalziel, J. R.; Carter, H. A.; Aubke, F. *Inorg. Chem* 1976, vol. 15, p. 1247; Stang, P. J.; Zhdankin, V. V.; Tykwinski, R. *Tetrahedron Lett.* 1991, vol. 32, p. 7497; Stang, P. J.; Zhdankin, V. V.; Tykwinski, R. Tetrahadron Lett. 1992, vol. 33, p. 1419; Stang, P. J.; Tykwinski, R.; Zhdankin, V. V. *J. Hetrocycl. Chem.* 1992, vol. 29, p. 815; and U.S. Pat. No. 5,277,767. According to Miller, R. D. U.S. Pat. No. 4,786,441: "The prior art methods of preparation involve an exchange reaction between lithium triflate and the corresponding onium halide with the reaction being an equilibrium one taking place in an aqueous or mixed aqueous-organic medium. There is no force driving the equilibrium reaction in either direction and in general, the process is inefficient." When sulfuric acid is used, the previously mentioned bisulfate salts are formed.

Exchange of the bisulfate counter ion for a more useful counter ion, such as hexafluorophosphate, trifluoromethanesulfonate (hereinafter referred to as "triflate"), or p-toluenesulfonate can be effected by treatment of the bisulfate with an aqueous mixture of, e.g., the sodium or potassium salt of the corresponding desired acid. However, this exchange reaction can present difficulties if the desired salt is somewhat soluble in the aqueous reaction mixture. In these cases the exchange reaction cannot be forced to completion by precipitation of the exchanged salt, and an undesirable mixture of salts is obtained. It is known in the art to treat diaryliodonium bisulfate salts with aqueous sodium chloride to obtain the corresponding chloride salt, which is quite insoluble in the reaction mixture, thus precipitating out of solution and forcing completion of the exchange reaction. Exchange of the chloride counter-ion to a more useful counter-ion such as the triflate can be effected by treatment with the corresponding desired acid (or silylester). (See Dektar, J. L., Hacker N. P., *J. Org. Chem.*, 1990, 55, 639; Research Disclosure RD 350042 1993; Beringer, F. M.; Drexler, E. M., Gindler, F. M., Lumpkin, C. C. *J. Am. Chem. Soc.*, 1953, vol. 75, p. 2705) This exchange reaction is forced to completion by the elimination of hydrochloric acid (or trimethylsilyl chloride). This process works well to prepare the desired diaryliodonium salts but it requires isolation of the diaryliodonium chloride and an additional exchange reaction.

Thus, there has not been provided a convenient, simple and safe process for the preparation of useful diaryliodonium triflate salts.

SUMMARY OF THE INVENTION

We have discovered a convenient, simple, safe and efficient one-pot method for the synthesis of diarlyiodonium fluoroalkyl sulfonate salts which does not involve sulfuric acid and which eliminates the need for any counter-ion exchange processes.

One aspect of the present invention is a novel method of making a diaryliodonium fluoroalkyl sulfonate salt comprising the steps of:

(a) forming a mixture comprising
  (i) an aromatic compound which is optionally substituted with one or more groups selected from the group consisting of electron-neutral groups, electron-donating groups, and combinations thereof, wherein the aromatic compound has at least one pendant —H, and wherein the aromatic compound is unreactive with a fluoroalkyl sulfonic acid(s) of element (b);
  (ii) an anhydride selected from the group consisting of aliphatic anhydrides, alicyclic anhydrides, and mixtures thereof, wherein the anhydride is optionally substituted with one or more groups unreactive with the fluoroalkyl sulfonic acid(s) of element (b), and wherein the anhydride is derived from an acid having a pka of greater than about 4.2;

(iii) an alkali metal salt of iodic acid; and (iv) optionally, a solvent which is unreactive with elements (i) to (iii);

(b) adding to the mixture, with agitation, the fluoroalkyl sulfonic acid of the formula $R^{11}$—$CF_2$—$SO_3H$, wherein $R^{11}$ is selected from the group consisting of alkyl groups, chlorofluoroalkyl groups, chlorinated alkyl groups, and fluorinated alkyl groups, wherein the fluoroalkyl sulfonic acid is optionally dissolved in a solvent which is unreactive with the fluoroalkyl sulfonic acid, such that reaction occurs but at a rate and a temperature selected to prevent an uncontrolled exothermic reaction; and (c) allowing the reaction to continue, with agitation, at a temperature selected to prevent uncontrolled exothermic reaction, to form diaryliodonium fluoroalkyl sulfonate salt.

The method of the invention optionally further comprises the step (d) of isolating the diaryliodonium fluoroalkyl sulfonate salt.

The present invention also provides the salts prepared according to the method of the invention.

Preferred salts prepared according to the method of the invention have a formula selected from the group consisting of

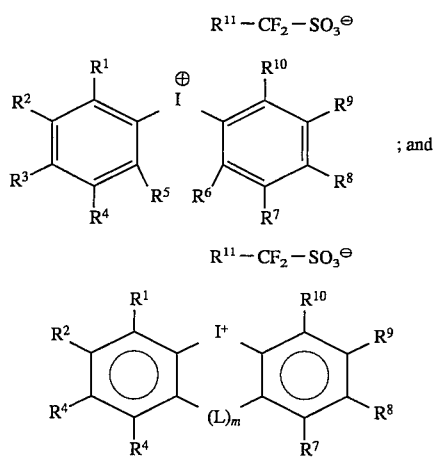

wherein m represents an integer of 0 or 1;

L is an electron neutral or electron donating group selected from the group consisting of —O—; —$NR^{12}$—, wherein $R^{12}$ represents —H or an alkyl group (typically as $C_{1-20}$ alkyl group); and —$(CR^{13}R^{14})_n$— wherein $R^{13}$ and $R^{14}$ each independently represents —H or an alkyl group or a substituted alkyl group and n represents an integer of 1 to 2;

$R^1$, $R^2$, $R^3$, $R^4$, $R^5$, $R^6$, $R^7$, $R^8$, $R^9$ and $R^{10}$ are each independently selected from the group consisting of electron neutral groups and electron donating groups;

wherein adjacent $R^1$, $R^2$, $R^3$, $R^4$, $R^5$, $R^6$, $R^7$, $R^8$, $R^9$, $R^{10}$ groups optionally may together form a ring; and $R^{11}$ is selected from the group consisting of halide groups, alkyl groups, chlorofluoroalkyl groups, chlorinated alkyl groups, and fluorinated alkyl groups.

Preferably, $R^1$, $R^2$, $R^3$, $R^4$, $R^5$, $R^6$, $R^7$, $R^8$, $R^9$ and $R^{10}$ are independently selected from the group consisting of:

alkyl groups comprising about 1 to about 20 carbon atoms;

halide groups;

substituted amino groups;

aromatic groups;

alkoxy groups;

aryloxy groups;

wherein each of said groups which $R^1$, $R^2$, $R^3$, $R^4$, $R^5$, $R^6$, $R^7$, $R^8$, $R^9$ and $R^{10}$ represent may optionally be substituted as long as the substituents do not substantially alter the overall electronic characteristics of the groups to which they are bonded (i.e., cause them to be electron withdrawing as defined above).

Examples of suitable halide groups include but are not limited to those selected from the group consisting of —F, —Cl, $CF_3$, —$CCl_3$, and —$C_2F_5$. Examples of suitable aromatic groups include but are not limited to those selected from the group consisting of phenyl, naphthyl, tolyl, xylyl, and mesityl. Examples of suitable alkoxy groups include but are not limited to those selected from the group consisting of methoxy, ethoxy, and isopropoxy. Examples of suitable substituted amino groups include but are not limited to those selected from the group consisting of alkyl substituted amino groups, carbonyl substituted amino groups, and sulfonyl substituted amino groups. Specific examples thereof include dimethylamino, diethylamino, piperidyl, and morpholino.

Preferably, the method of the invention consists essentially of the steps (a)–(c) and most preferably consists of the steps (a)–(d). Preferably the mixture of element (c) consists essentially of (i)–(iv), most preferably consists of (i)–(iv).

Another aspect of the present invention is a novel diaryliodonium sulfonate salt having the formula:

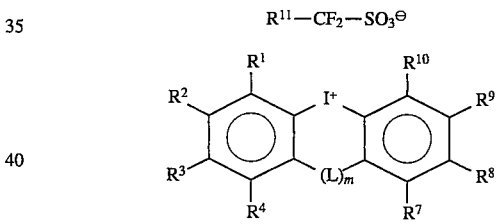

wherein m, L, $R^1$, $R^2$, $R^3$, $R^4$, $R^7$, $R^8$, $R^9$, $R^{10}$ and $R^{11}$ are as defined above.

DETAILED DESCRIPTION OF THE INVENTION

The method of the invention involves the reaction of the following components: an electron-neutral and/or electron-rich aromatic compound, an anhydride, an alkali metal salt of iodic acid, a fluoroatkyl sulfonic acid, and, optionally, a solvent unreactive towards the fluoroalkyl sulfonic acid.

Aromatic Compounds

Aromatic compounds suitable for use in the method of the invention are selected from the group consisting of unsubstituted aromatic compounds and aromatic compounds bearing only electron-neutral and/or electron-rich (electron-donating) substituents, wherein the aromatic compound has at least one unsubstituted position (i.e. at least one —H). Mononuclear and polynuclear (bicyclic, tricyclic, etc.) aromatic compounds are useful herein. Examples of useful aromatic compounds include but are not limited to those selected from the group consisting of benzene, cumene, cymene, mesitylene, toluene, xylene, napthalene, fluorene, phenanthrene, and mixtures thereof. The aromatic compound must not bear any electron withdrawing groups such as —$NO_2$, —$CO_2H$, —CN, —$CF_3$, —$SO_2H$, —$SO_2R$ (wherein R is an alkyl or aryl group), —SOR (wherein R is an alkyl group or aryl group), etc. One skilled in the art will readily recognize those substituents which are electron-withdrawing and those which are electron-rich or electron-neutral. In the present context, "electron-donating" and "electron-rich are used interchangeably, and refer to substituents whose "sigma plus" value is less than 0.48. In the present context, "electron-withdrawing" refers to substituents whose "sigma plus" value is 0.48 or greater. The "sigma plus" value is a well understood term by those skilled in the art and is further described in Ritchie, C. D.; Sager, W. F. Prog. Phys. Org. Chem 1964, 2, 323. Examples of electron-neutral or electron-rich substituents which may be present on the aromatic rings include, but are not limited to those selected from the group consisting of (a) $C_1$ to $C_{20}$ alkyl groups, wherein the alkyl groups may be linear, branched, or (poly) cyclic, and may themselves bear substituents as long as those substituents do not substantially alter the electronic characteristics of the alkyl group(s); (b) halide groups selected from the group consisting of fluoride, chloride, bromide, and iodide groups; (c) aryl substituted, alkyl substituted, and unsubstituted amino groups including but not limited to those selected from the group consisting of N,N-dialkyl amino, N,N-diaryl amino, and heterocyclic amino groups wherein the heterocyclic amino group is bonded to the aromatic compound via the heterocyclic ring nitrogen, and including amino groups wherein the alkyl and/or aryl groups on the nitrogen atoms may themselves bear substituents as long as those substituents do not substantially alter the overall electronic characteristics of the amino group(s) and/or the heterocyclic amino group(s); (d) aromatic groups including but not limited to those selected from the group consisting of phenyl cumyl, cymyl, mesityl, tolyl, xylyl, naphthyl, fluorenyl, and phenanthrenyl; and (e) alkoxy moieties wherein the alkyl substituents on the oxygen atoms may themselves bear substituents so long as those substituents do not substantially alter the overall electronic characteristics of the ether groups. In the present context, substituents "do not substantially alter the overall electronic characteristics of the group" when the sigma plus value of the substituent is less than 0.48.

Preferably, the aromatic compound is either unsubstituted or is substituted with one alkyl substituent selected from the group consisting of about $C_1$ to about $C_{20}$ alkyl groups, wherein the alkyl groups may be linear, branched or (poly) cyclic, and may themselves bear non-carbon substituent(s) as long as those substituent(s) do not substantially alter the electron characteristics of the alkyl group. It must be noted that a greater amount of fluoroalkyl sulfonic acid must be used according to the method of the invention if the aromatic compounds have substituted amino groups.

Examples of specific aromatic compounds useful according to the method of the invention include but are not limited to diaryl compounds of the formula Ar—$(L)_m$—Ar, wherein Ar represents a substituted or unsubstituted aromatic group including but not limited to those selected from the group consisting of phenyl, naphthyl, cumyl, cymyl, mesityl, tolyl, xylyl, fluorenyl, and phenanthrenyl; m represents an integer of 0 to 1; and L is a divalent linking group selected from the group consisting of —$(CR^{13}R^{14})_n$—, wherein $R^{13}$ and $R^{14}$ are independently selected from the group consisting of —H and alkyl groups (preferably $C_1$–$C_{20}$), and wherein n is an integer selected from the group consisting of 1 and 2 (if n was 3 or greater a low yield would result); —O—; $NR^{12}$— wherein $R^{12}$ is selected from the group consisting of —H and alkyl groups (preferably $C_1$–$C_{20}$).

Such diaryl compounds also form cyclic iodonium salts, wherein the iodine atom is one member of a central five-membered, six-membered or seven-membered ring.

Diarylalkyl compounds particularly useful according to the invention include gem-diaryl compounds such as 1,1-diarylalkyls wherein the aryl moieties are as defined above. Alkyls of this group may be of any chain length from about 1 to about 20 carbon atoms, and may be linear, branched, or (poly) cyclic, and may themselves bear substituents as long as those substituents do not substantially alter the electronic characteristics of the alkyl group(s). Iodonium salts of 1,1-diarylalkyls of the invention form cyclic iodonium salts, wherein the iodine atom is one member of a central six-membered ring, provided the aromatic rings are both substituted in the para positions.

Anhydrides

Anhydrides useful according to the invention are derived from acids which have pkas of about 4.2 or greater, for reasons of good yield, preferably, about 4.5 to about 5.0 for reasons of even better yield and commercial availability. Anhydrides derived from acids which have pkas less than 4.2 result in a poor yield.

Anhydrides useful in the method of the invention are selected from the group consisting of (substituted) aliphatic anhydrides including but not limited to those selected from the group consisting of acetic anhydride, propionic anhydride, butyric anhydride, pentanoic, anhydride, hexanoic anhydride, heptanoic anhydride, octanoic anhydride, decanoic anhydride; (substituted) alicyclic anhydrides including but not limited to, those selected from the group consisting of succinic anhydride, glutaric anhydride, adipic anhydride; and mixtures thereof. Suitable substituents would include those that are unreactive with the other mixture components under reaction conditions. (They should be unreactive with fluoroalkane sulfonic acid.) Examples of suitable substituents include but are not limited to those selected from the group consisting of alkyl, alkoxyl, aryl, halides, etc. Examples of specific suitable substituents include methyl, ethyl, propyl, chloro, bromo, iodo, fluoro, methoxy, ethoxy, aryl, dimethylamino, diethylamine, etc. Unsuitable substituents include those such as alcohols, mercaptans, olefins, acetylenes, primary amines, etc. One skilled in the art would be capable of recognizing those substituents which would be reactive with fluoroalkane sulfonic acid and those which would be unreactive. Preferably, the anhydride is acetic anhydride for reasons of availability.

Alkali Metal Salts of Iodic Acid

As used herein the term "alkali metal" refers to sodium, potassium, lithium, and cesium. Alkali metal salts of iodic acid ("alkali iodates") are a convenient source of iodate for the subject reaction, since the salts dissociate easily and the iodate ion readily displaces hydrogen from aromatic nuclei in electrophilic substitution reactions under acidic reaction conditions. Alkali metal salts useful in the method of invention are selected from the group consisting of potassium iodate, sodium iodate, lithium iodate, cesium iodate, and mixtures thereof. Potassium iodate is preferred because of its availability and ease of handling. In the stoichiometry of the reaction, one-half equivalent of alkali iodate is preferably used for each equivalent of aromatic compound when the aromatic compound is not a diaryl compound such as a gem-diaryl compound. In the latter case, one equivalent of alkali iodate is preferably used for each equivalent of diaryl compound. In cases where the aromatic compound may be expensive or of limited availability, an excess of alkali iodate may be used to ensure relative completeness of the reaction.

Fluorinated Alkyl Sulfonic Acids

Fluoroalkyl sulfonic acids of the formula $R^{11}$—$CF_2$—$SO_3H$ are useful according to the method of the invention, wherein $R^{11}$ is selected from the group consisting of alkyl groups (typically $C_{1-20}$), chlorofluoro alkyl groups (typically $C_{1-20}$), chlorinated alkyl groups (typically $C_{1-20}$), and fluorinated alkyl groups (typically $C_{1-20}$). Preferably perfluoroalkyl groups are present (i.e. perfluoroalkane sulfonic acids). Fluoroalkyl sulfonic acids useful according to the method of the invention provide the sulfonate counterion for the iodonium moiety. Perfluoroalkyl sulfonic acids are described in the *Encyclopedia of Chemical Technology*, 3rd Edition, Volume 10, pp. 952–955, which reference is incorporated by reference herein. Perfluoroalkyl sulfonic acids have the general formula $R_fSO_3H$, wherein $R_f$ represents a perfluorinated alkyl moiety. Preferably $R_f$ represents a perfluorinated alkyl moiety having from about 1 to about 20 carbon atoms, more preferably about 1 to about 10 carbon atoms, for reasons of availability and may constitute a straight chain moiety, a branched chain moiety, or a cyclic moiety. Examples of such acids include but are not limited to those selected from the group consisting of $CF_3CO_3H$, $C_2F_5SO_3H$, n-$C_4F_9SO_3H$, n-$C_5F_{11}SO_3H$, n-$C_6F_{13}SO_3H$, n-$C_8F_{17}SO_3H$,

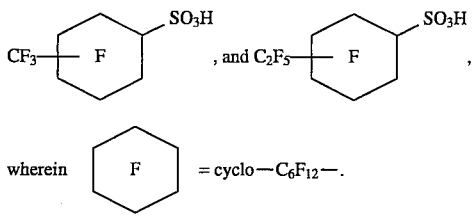

wherein $\boxed{F}$ = cyclo—$C_6F_{12}$—.

Preferably, trifluoromethanesulfonic acid, commonly referred to as "triflic acid," is used according to the method of the invention for reasons of cost and availability.

Optional Solvents

Optionally, a solvent (typically an organic solvent) which is unreactive towards the fluoroalkyl sulfonic acid(s) used and which is itself unreactive under the reaction conditions employed (i.e. strongly acidic and oxidative conditions) may be used according to the method of the invention. Examples of such unreactive solvents include but are not limited to those selected from the group consisting of hydrocarbons, including but not limited to those selected from the group consisting of hexane, pentane, heptane, cyclohexane, octane, mixtures thereof, etc.; chlorinated hydrocarbons, including but not limited to those selected from the group consisting of dichloromethane, chloroform, carbon tetrachloride, dichloroethane, trichloroethane, tetrachloroethane, mixtures thereof, etc.; fluorinated hydrocarbons such as freons; carboxylic acids, including but not limited to those selected from the group consisting of acetic acid, propionic acid, butyric acid, etc. and, we theorize, inorganic solvents such as $SO_2$ and carbon disulfide. Organic solvents are readily available, unreactive, and have good solubility properties. If an organic solvent is used, the preferred solvent is dichloromethane for reasons of its unreactiveness and solubilizing ability. Inorganic solvents may be useful but would be more difficult to use. In practice, most of the reactants employed in the method of the present invention are liquids and thus solvent may be included but is not necessary in such situations. A solvent is typically added to aid in dissolving the aromatic compounds of the reaction mixture when such aromatic compounds are solids.

Description of the Reaction

The stoichiometry of the reaction requires two equivalents of an aromatic compound (or one equivalent of a diaryl compound), two equivalents of an anhydride, one equivalent of an alkali metal salt of iodic acid and two equivalents of a fluoroalkyl sulfonic acid.

Typically the reaction of the invention involves the use of about 2 to about 10 equivalents of an aromatic compound, about 1 to about 4 equivalents of an anhydride, about 0.5 to 2 equivalents of an alkali metal salt of iodic acid, 0 to about 100% weight of a solvent based upon the weight of the aromatic compound, and about 1 to 3 equivalents of fluoroalkyl sulfonic acid.

Preferably the reaction of the invention involves the use of about 2 to about 3 equivalents of aromatic compound, about 2 to 3 equivalents anhydride, about 1 to 1.5 equivalents of an alkali metal salt of iodic acid, 0 to about 50% weight of a solvent, and about 1.9 to about 2.5 equivalents of fluoroalkyl sulfonic acid.

If too much fluoroalkane sulfonic acid is used the yield of the reaction may be decreased because of the formation of by-products. If too little fluoroalkane sulfonic acid is used the yield of the reaction relative to the alkali metal salt of the iodic acid will decrease. If too much aromatic compound is used the yield of the iodonium triflate relative to the aromatic compound is reduced. If too little aromatic compound is used the yield of the iodonium triflate relative to the aromatic compound is increased.

If too much anhydride is used the yield relative to the anhydride decreases. If too little anhydride is used the yield relative to the anhydride increases.

If too much alkali metal salt of iodic acid is used the yield relative to the alkali metal salt of iodic acid decreases. If too little alkali metal salt of iodic acid is used the yield relative to the alkali metal salt of iodic acid increases.

If too little solvent is used and the aromatic compound (or diaryl compound) is a solid the yield may be reduced. If too much solvent is used the yield of the reaction may be reduced.

The method of the invention involves forming a mixture by combining in any order the aromatic compound, the anhydride, the alkali metal salt of iodic acid, and optional solvent in a suitable reaction vessel such a pyrex or glass lined vessel, due to the acidic conditions. The components are typically combined at a temperature of 0° C. to 25° C. (most typically 25° C.), one atmosphere pressure, and medium agitation (typically about 80 rpm). The temperature of combination should be high enough to facilitate reaction but below the boiling point of any one component.

Typically a mixture of at least about 2 equivalents of a suitable aromatic compound and 1 equivalent of alkali metal iodate in an anhydride such as acetic anhydride is stirred and cooled to typically about −10° C. to 25° C. (preferably about 20° C. or less) and treated with at least 2 equivalents (typically a slight excess, i.e. about 10–20% more) of fluoroalkane sulfonic acid at such a rate as to keep the reaction at a temperature selected to prevent uncontrolled exotherm and maximize yield (typically about 25° C. or below). When addition is complete, the reaction mixture is stirred typically for about 10 to 14 hours at typically about 20° C. to about 40° C. (preferably about 30° C. to about 40° C.) while the reaction continues until the end product is formed and the reaction is at least substantially completed (typically at least about 80% complete, preferably at least about 90% complete). Usually the reaction product contains a few impurities, typically up to about 10% impurities.

The salt may be isolated from the reaction mixture. By isolating it is meant removing some or all of any remaining components other than the diaryliodonium fluoroalkyl sulfonate salt. These components include unreacted starting materials, reaction by-products and solvents.

The resultant reaction mixture is carefully diluted with water (since the resultant reaction mixture contains acid), while maintaining the temperature at or below about 25° C. The desired diaryliodonium fluoroalkyl sulfonate salt is typically isolated from the aqueous phase by admixture with an organic solvent, such as dichloromethane, toluene, ethyl acetate, etc. which may effect precipitation or solution of the salt. If the salt precipitates it is collected by filtration and optionally recrystallized. If the salt remains in the organic solvent, the aqueous phase is removed. The organic phase is optionally extracted with water to remove residual impurities. The organic phase is optionally concentrated in vacuo and the resulting residue is optionally recrystallized.

If the temperature is less than about 20° C. the reaction rate will be slow and the yield low. If the temperature is greater than about 40° C. the product could decompose.

Linear diaryliodonium perfluoroalkane sulfonates of the invention are prepared as follows: A mixture of at least about 2 equivalents of a suitable aromatic compound that cannot form a cyclic iodonium salt by bridging 2 of the aryl groups or 1 equivalent of suitable diaryl compound that can form a cyclic iodonium salt by bridging 2 of the aryl groups, and 1 equivalent of alkali metal iodate in an anhydride such as acetic anhydride is stirred and cooled to typically about −10° C. to about 25° C. (more typically about 20° C. or less) and treated with at least 2 equivalents (typically a slight excess, i.e. about 10–20% more) of fluoroalkane sulfonic acid at such a rate as to keep the reaction at a temperature selected to prevent uncontrolled exotherm and maximize yield (typically about 25° C. or below). When addition is complete, the reaction mixture is stirred for about 10 to about 14 hours at room temperature (typically about 20° C. to about 40° C.) while the reaction continues until the end product is formed and the reaction is at least substantially completed (at least about 80% complete). The resultant reaction mixture is carefully diluted with water (since the resultant reaction mixture contains acid), keeping the reaction temperature at or below about 25° C. The desired diaryliodonium fluoroalkyl sulfonate salt is typically isolated from the aqueous phase by admixture with an inert solvent, such as dichloromethane, which may effect precipitation or solution of the salt. Acyclic products obtained from monosubstituted aromatics are a mixture of the para-para and ortho-para isomers.

EXAMPLES

The invention is further illustrated by the following nonlimiting examples. All parts, percentages, ratios, etc. in the examples and the rest of the specification are by weight unless otherwise specified.

Example 1 - Preparation of 2, 3, 7, 8, 10-pentamethyl- 10H-dibenzo[b,e]iodimium trifluoromethanesulfonate.

Into a 250 mL 3-necked round bottom flask equipped with a mechanical stirrer, thermometer, and inlet was charged, with agitation, 30.0 grams (125.8 mmol 1.0 eq) of 1,1-bis(3, 4-dimethylphenyl)ethane, 45 mL of acetic anhydride and 26.9 grams (126 mmol, 1.0 eq) of potassium iodate to form a mixture which was cooled to −10° C. Trifluoromethanesulfonic acid (also referred to herein as "triflic acid" (37.8 grams, 22.3 mL, 252 mmol, 2.0 eq) was added dropwise to the flask at such a rate that the reaction temperature did not exceed 0° C. The mixture was stirred at 0° C. and allowed to warm to room temperature overnight. The reaction mixture was black with a thick precipitate. To the mixture was added approximately 8 mL of water at or below 25° C. followed by methylene chloride. The precipitate that formed was collected and washed with methylene chloride, water, and acetone to give 12.53 grams of crude product. This material was recrystallized from approximately 750 mL of acetone to give 4.71 grams (10% yield) of product having a melting point of 290° C. (decomposes on melting).

Example 2 - Preparation of Ditolyliodonium Trifluoromethanesulfonate.

Into a 2 liter 3-necked round bottom flask equipped with a mechanical stirrer, thermometer, and inlet was charged with agitation 230.394 g (1076.60 mmol) of potassium iodate, 400 g (4341.13 mmol) of toluene and 360 mL of acetic anhydride. The mixture was cooled to −15° C. Trifluoromethanesulfonic acid (325.751 g, 2170.57 mmol) was added dropwise at a rate such that the temperature remained below 5° C. The addition was complete in 2.5 hours. The mixture was allowed to stir for 4 hours at 0° C. The cooling bath was removed and stirring was continued overnight. The mixture was cooled to 0° C. and 537 mL of water was added at such a rate that the temperature remained below 10° C. Dichloromethane (500 mL) was added and the mixture was stirred 30 minutes and allowed to phase split. The dichloromethane phase was separated. To the aqueous phase was added 500 mL of dichloromethane and the mixture was stirred for 30 minutes and allowed to phase split. The dichloromethane phase was separated. The combined dichloromethane phases were concentrated in vacuo at 40° C. to give a brown liquid. Isopropyl ether (800 mL) was added and the mixture was stirred for one hour. The resulting solid was collected by filtration and washed with 800 mL of isopropyl ether. To the solid was added 460 mL of isopropyl alcohol and the mixture was heated to 82° C. for 30 minutes or until the solid dissolved. The solution was diluted with 460 mL of hexane and the mixture was cooled to 0° C. The resulting solid was collected by filtration and washed with a mixture of 200 mL of hexane and 200 mL of isopropyl alcohol. The solid was heated with 460 mL of isopropyl alcohol at 82° C. for 30 minutes or until a homogeneous solution was obtained. The solution was diluted with 460 mL of hexane and the mixture was cooled to 0° C. The solid was collected by filtration and washed with a mixture of 200 mL of hexane and 200 mL of isopropyl alcohol. The solid was then washed with 300 mL of hexane and allowed to air dry to give a white solid (213.92 grams, 43.5% yield, melting point 110–127).

Example 3 - Preparation of Di(dodecylphenyl)iodonium Trifluoromethanesulfonate.

Into a 250 ml 3-neck round bottom flask equipped with a mechanical stirrer, thermometer, and inlet was charged, with agitation, 8.67 grams (40.6 mmol, 0.5 eq) of potassium iodate, 20.0 grams (18.2 mmol, 1.0 eq) of dodecylbenzene, and 40 mL of acetic anhydride to form a mixture. To the mixture was added 12.2 grams (7.19 mL, 81.2 mmol, 1.0 eq) of triflic acid at 0° C. dropwise at such a rate that the reaction temperature did not exceed 0° C. The reaction mixture was allowed to slowly warm to room temperature over about a 14 hour period and then quenched with 20 mL of water at 0° C. while agitation continued. The mixture was extracted with methylene chloride and the methylene chloride layer was washed with sodium bicarbonate until neutral. The methylene chloride layer was concentrated in vacuo and slowly began to thicken. This material was dissolved in approximately 600 mL of hexanes and cooled in dry ice. A precipitate formed and the mixture was filtered and washed with cold hexanes. The precipitate was collected to give 4.9 grams of a waxy flaky solid (13% yield).

Example 4 - Preparation of 4,4'-Di-t-butylbiphenyl.

Into a 250 ml 3-neck round bottom flask equipped with a mechanical stirrer, thermometer, and inlet was charged, with agitation, 40 mL of nitromethane to which was added portionwise 20.7 grams (156 mmol, 1.69 eq) of aluminum chloride with agitation and cooling so as not to exceed 40° C. This solution was added to a mixture of 14.2 grams (92.1 mmol, 1.0 eq) of biphenyl and 26.5 grams (120 mmol, 1.3 eq) of 2,6-di-t-butyl-4-methylphenol in 40 mL of nitromethane at 15° C. over a period of 5 to 10 minutes. The mixture turned a dark opaque color and near the end of the addition, the mixture became very thick. The reaction mixture was allowed to stir for 30 minutes and then poured into ice-water. The mixture was extracted with ether twice and the ether layer was concentrated in vacuo. Additional ether was added to the solid and the mixture was concentrated in vacuo. Toluene was added to the solid and the mixture was concentrated in vacuo. This treatment was to insure removal of nitromethane before washing with base. The brown solid residue was dissolved in ether and washed with approximately 300 mL of 1M sodium hydroxide until the aqueous layer was no longer deeply colored. The organic layer was washed with water and concentrated in vacuo. The brown residue was recrystallized from approximately 150 mL of ethanol to give 10 grams (41% yield). Melting point= 129°–130° C.

Example 5 - Preparation of 3,7-Di-t-butyldibenziodolium Trifluoromethanesulfonate.

Into a 250 ml 3-neck round bottom flask equipped with a mechanical stirrer, thermometer, and inlet was charged with agitation, 4.0 grams (18.8 mmol, 1.0 eq) of potassium iodate, 5.0 grams (18.8 mmol, 1.0 eq) of 4,4'-di-t-butylbiphenyl, and 20 mL of acetic anhydride to form a mixture which was cooled to 0° C. To the mixture was added 5.63 grams (3.32 mL, 37.5 mmol, 2.0 eq) of triflic acid dropwise at such a rate that the reaction temperature did not exceed 10° C. The temperature was kept below 10° C. during the addition by the use of a cooling bath. The reaction mixture was never homogeneous and the 4,4'-di-t-butylbiphenyl did not appear very soluble in the reaction mixture. The reaction mixture turned dark almost immediately upon addition of the triflic acid. The mixture was stirred for about 14 hours at room temperature. The reaction was quenched with approximately 60 mL of water and extracted with methylene chloride. The methylene chloride layer was washed with saturated aqueous sodium bicarbonate solution and concentrated in vacuo. The residue was a dark viscous oil. This material was soluble in ether and could be precipitated with hexanes; however, the precipitate was a brown amorphous powder. Titration with acetone gave a tan solid 0.2 gram (2% yield). Melting point=233°–234° C.

Example 6 - Preparation of 1,1-Bis(4-t-butylphenyl)heptane.

Into a 250 ml 3-neck round bottom flask equipped with a mechanical stirrer, thermometer, and inlet was charged, with agitation, 34 mL of nitromethane to which was added portionwise 17.8 grams (134 mmol, 1.7 eq) of aluminum chloride to form a solution with cooling such that the temperature did not exceed 40° C. This solution was added to a mixture of 20.0 grams (79.2 mmol, 1.0 eq) of 1,1-diphenylheptane and 22.8 grams (103 mmol, 1.3 eq) of 2,6-di-t-butyl-4-methylphenol in 56 mL of nitromethane at 15° C. over a period of 5 to 10 minutes. The mixture turned a dark opaque color. The reaction mixture was allowed to stir for 30 minutes at room temperature and was then poured into ice-water. The mixture was extracted with ether twice and the ether layer was concentrated in vacuo. Additional ether was added to the residue and concentrated followed by addition of toluene and concentration. This treatment was to insure removal of the nitromethane before washing with base. The dark oil was dissolved in ether and washed with approximately 400 mL of 1 M sodium hydroxide. The aqueous layer was less highly colored. The organic layer was washed with water and concentrated in vacuo. The residue was distilled in vacuo (1.5–2 mmHg). A forerun of 2,6-di-t-butyl- 4-methylphenol was collected. Boiling point 75°–105° C. at 2 mm (Literature Boiling Point=265° C. at 760 mm). The second fraction gave the 15.0 grams product, (55% yield). Boiling point=195°–197° C. at 2 mm.

Example 7 - Preparation of 3,7-Di-t-butyl-10-hexyl-10H-dibenzo[b,e]iodonium Trifluoromethanesulfonate.

Into a 150 ml 3-neck round bottom flask equipped with a mechanical stirrer, thermometer, and inlet was charged, with agitation, 2.9 grams (13.7 mmol, 1.0 eq) of potassium iodate, 5.0 grams (13.7 mmol, 1.0 eq) of 1,1-Bis(4-t-butylpheny) heptane, and 8 mL of acetic anhydride to form a mixture which was cooled to 0° C. To the mixture was added 4.1 grams (2.4 mL, 27 mmol, 2.0 eq) of triflic acid dropwise at such a rate that the reaction temperature did not exceed 0° C. This mixture became thick during the addition. The mixture was stirred at 0° C. and allowed to warm to room temperature over about 14 hours. Approximately 10 mL of water was added to the reaction mixture at 0°–20° C. followed by methylene chloride. The precipitate dissolved in the methylene chloride and the organic phase was washed with water, sodium bicarbonate, and water, and concentrated in vacuo to give a viscous dark amber oil. This material was stirred with hexanes for 3 days and a brown solid residue was collected to give 0.88 gram (10% yield).

Example 8 - Preparation of Di(4-chlorophenyl)iodonium Trifluoromethanesulfonate.

To a mixture of 20.0 grams (178 mmol, 1 eq) of chlorobenzene in 30 mL of acetic anhydride and 19.0 grams (88.8 mmol, 0.5 eq) of potassium iodate cooled to 0° C. was added 26.7 grams (15.7 mL, 178 mmol, 1.0 eq) of triflic acid at such a rate that the reaction temperature did not exceed 0° C. The mixture was allowed to warm to room temperature slowly and stirred for 14 hours. Approximately 45 mL of water was added to the reaction mixture at 0°–20° C. followed by methylene chloride. The precipitate dissolved in the methylene chloride and the organic phase was washed with water, aqueous sodium bicarbonate, and water, and concentrated in vacuo. This material was recrystallized from a mixture of 20 mL of isopropanol and 35 mL of hexane to give 7.62 grams (8.6% yield). A second crop was obtained from the mother liquor, 2.5 grams (total yield 11.4%). The product contains less than 7% of the isomeric 2-chlorophenyl-4-chlorophenyliodonium triflate and a small amount of uncharacterized impurity.

Example 9 - Preparation of 1,1-Bis(4-t-butylphenyl)methane.

A solution of 13.4 grams (100 mmol, 1.69 eq) of anhydrous aluminum chloride in 26 mL of nitromethane was prepared by slowly adding the aluminum chloride to the nitromethane with cooling at 0° C. This solution was added to a mixture of 10.0 grams (59.4 mmol, 1.0 eq) of diphenylmethane and 17.1 grams (77.3 mmol, 1.3 eq) of 2,6-di-t-butyl-4-methytphenol in 28 mL of nitromethane at 15° C. over a period of 5 to 10 minutes. The mixture turned to a dark opaque color. The reaction mixture was allowed to stir for 30 minutes at room temperature and then poured into ice-water. The mixture was extracted twice with ether and the ether layer was concentrated in vacuo. Additional ether was added to the residue and concentrated, followed twice by addition of toluene and concentration. This treatment was to insure removal of the nitromethane before washing with base. The dark oil was dissolved in ether and washed with 1L of 1 M potassium hydroxide until the aqueous layer was no longer colored. Then the mixture was washed with water and concentrated in vacuo. The product was collected at 134°–150° C./0.25 mmHg (12.2 grams, 73% yield).

Example 10 - Preparation of 3,7-di-t-butyl-10H-dibenzo[b,e]iodinium Trifluoromethanesulfonate.

To a mixture of 5.0 grams (17.8 mmol, 1.0 eq) of 1,1-bis(4-t-butylphenyl)methane in 8 mL of acetic anhydride and 3.8 grams (17.8 mmol, 1.0 eq) of potassium iodate cooled to 0° C. was added 5.3 grams (3.2 mL, 36 mmol, 2.0 eq) of triflic acid at such a rate that the reaction temperature did not exceed 0° C. This mixture became thick during the addition. The mixture was stirred at 0° C. and allowed to warm to room temperature overnight. Approximately 10 mL of water was added to the reaction mixture at 0°–20° C. followed by methylene chloride. The precipitate dissolved in the methylene chloride and the organic phase was washed with water, aqueous sodium bicarbonate, and water, and concentrated in vacuo to give a dark solid. This material was triturated with approximately 10 mL of ether and then washed with an additional 10 mL of ether. The residue was then triturated with approximately 20 mL of methylene chloride to give 1.0 grams (10% yield) of product. This material was stable to over 280° C.

Various modifications and alterations of this invention will become apparent to those skilled in the art without departing from the scope and spirit of this invention, and it should be understood that this invention is not to be unduly limited to the illustrative embodiments set forth herein.

We claim:

1. A method of making a diaryliodonium fluoroalkyl sulfonate salt consisting essentially of the steps of:
   (a) forming a mixture consisting essentially of
      (i) an aromatic compound which is optionally substituted with one or more groups selected from the groups consisting of electron-neutral groups, electron-donating groups, and combinations thereof, wherein the aromatic compound has at least one pendant —H, and wherein said aromatic compound is unreactive with a fluoroalkyl sulfonic acid(s) of element (b);
      (ii) an anhydride selected from the group compsisting of aliphatic anhydrides, alicyclic anhydrides, and mixtures thereof, wherein the anhydride is optionally substituted with one or more groups unreactive with the fluoroalkyl sulfonic acid(s) of element (b), and wherein the anhydride is derived from an acid having a pka of greater than about 4.2;
      (iii) an alkali metal salt of iodic acid; and
      (iv) optionally, a solvent which is unreactive with elements (i) to (iii);
   (b) adding to the mixture, with agitation, the fluoroalkyl sulfonic acid of the formula $R^{11}$—$CF_2$—$SO_3H$, wherein $R^{11}$ is selected from the group consisting of alkyl groups, chlorofluoroalkyl groups, chlorinated alkyl groups, and fluorinated alkyl groups, wherein the fluoroalkyl sulfonic acid is optionally dissolved in a solvent which is unreactive with the fluoroalkyl sulfonic acid, such that reaction occurs but at a rate and a temperature selected to prevent an uncontrolled exothermic reaction;
   (c) allowing the reaction to continue, with agitation, at a temperature selected to prevent uncontrolled exothermic reaction, to form diaryliodonium fluoroalkyl sulfonate salt.

2. The method of claim 1 which further comprises a step
   (d) of isolating the diaryliodonium fluoroalkyl sulfonate salt.

3. The method of claim 1 wherein said aromatic compound is selected from the group consisting of benzene, alkyl substituted benzene compounds, and aryl substituted benzene compounds.

4. The method of claim 1 wherein said aromatic compound is selected from the group consisting of benzene, toluene, xylene, ethyl benzene, tert-butylbenzene, isopropylbenzene, cyclohexylbenzene, and dodecylbenzene.

5. The method of claim 1 wherein said aromatic compound is selected from the group consisting of diaryl compounds of the formula Ar—$(L)_m$—Ar, wherein Ar represents a substituted or unsubstituted aromatic group m represents an integer of 0 to 1; and L is a divalent linking group selected from the group consisting of —$(CR^{13}R^{14})_n$—, wherein $R^{13}$ and $R^{14}$ are each independently selected from the group consisting of —H and alkyl groups, and wherein n is an integer selected from the group consisting of 1 and 2; —O—; —$NR^{12}$— wherein $R^{12}$ is selected from the group consisting of —H and alkyl groups.

6. The method of claim 1 wherein the anhydride has a pKa of about 4.5 to about 5.0.

7. The method of claim 1 wherein the anhydride is selected from the group consisting of acetic anhydride, propionic anhydride, butyric anhydride, pentanoic anhydride, hexanoic anhydride, heptanoic anhydride, octanoic anhydride, decanoic anhydride, succinic anhydride, glutaric anhydride, adipic anhydride, and mixtures thereof.

8. The method of claim 1 wherein said alkali metal salt of iodic acid is selected from the group consisting of potassium iodate, sodium iodate, lithium iodate, cesium iodate, and mixtures thereof.

9. The method of claim 1 wherein said fluorinated alkyl sulfonic acid is a perfluoroalkane sulfonic aid.

10. The method of claim 1 wherein said fluorinated alkyl sulfonic acid is selected from the group consisting of $CF_3SO_3H$, $C_2F_5SO_3H$, n-$C_4F_9SO_3H$, n-$C_5F_{11}SO_3H$, n-$C_6F_{13}SO_3H$, n-$C_8F_{17}SO_3H$,

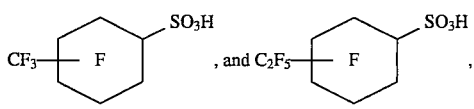

wherein  = cyclo—$C_6F_{12}$—.

11. The method of claim 1 wherein the optional solvent is an organic solvent.

12. The method of claim 1 which involves the use of two equivalents of an aromatic compound or one equivalent of a diaryl compound, two equivalents of an anhydride, one equivalent of an alkali metal salt of iodic acid and two equivalents of a fluoroalkyl sulfonic acid.

13. The method of claim 1 which involves the use of about 2 to about 10 equivalents of the aromatic compound, about 1 to about 4 equivalents of the anhydride, about 0.5 to 2 equivalents of the alkali metal salt of iodic acid, 0 to about 100% weight of the solvent based upon the weight of the aromatic compound, and about 1 to 3 equivalents of fluoroalkyl sulfonic acid.

14. The method of claim 1 which involves the use of about 2 to about 3 equivalents of the aromatic compound, about 2 to 3 equivalents of the anhydride, about 1 to 1.5 equivalents of the alkali metal salt of iodic acid, 0 to about 50% weight of the solvent, and about 1.9 to about 2.5 equivalents of the fluoroalkyl sulfonic acid.

15. The method of claim 1 wherein said anhydride is acetic anhydride.

16. The method of claim 1 wherein said fluoroalkyl sulfonic acid is trifluoromethane sulfonic acid.

* * * * *

UNITED STATES PATENT AND TRADEMARK OFFICE
CERTIFICATE OF CORRECTION

PATENT NO.: 5,488,147

DATED: January 30, 1996

INVENTOR(S): Dennis E. Vogel and Kim M. Vogel

It is certified that error appears in the above-identified patent and that said Letters Patent is hereby corrected as shown below:

Col. 3, line 41, the chemical structure should be:

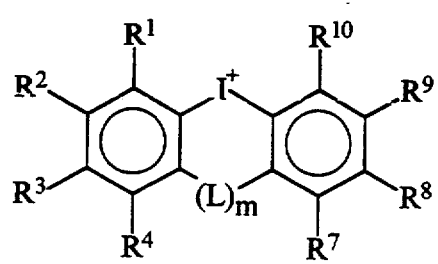

Col. 3, line 61, delete "$R^5$, $R^6$,".

Col. 14, line 1, "compsisting" should be --consisting--.

Signed and Sealed this

Twenty-third Day of July, 1996

Attest:

BRUCE LEHMAN

*Attesting Officer*     Commissioner of Patents and Trademarks